United States Patent [19]

Martin

[11] Patent Number: 4,683,883

[45] Date of Patent: Aug. 4, 1987

[54] TWO-PIECE HEART VALVE HOLDER/ROTATOR

[75] Inventor: Richard L. Martin, Austin, Tex.

[73] Assignee: Hemex Scientific, Inc., Austin, Tex.

[21] Appl. No.: 728,836

[22] Filed: Apr. 30, 1985

[51] Int. Cl.$^4$ .......................... A61F 2/24; A61B 17/00
[52] U.S. Cl. ..................................... 128/303 R; 623/2
[58] Field of Search ................... 128/321, 345, 303 R; 623/2

[56] References Cited

U.S. PATENT DOCUMENTS

| | | | |
|---|---|---|---|
| 3,587,115 | 6/1971 | Shiley | 623/2 |
| 3,628,535 | 12/1971 | Ostrowsky et al. | 128/303 |
| 3,828,787 | 8/1974 | Anderson et al. | 128/303 R |
| 3,860,005 | 1/1975 | Anderson et al. | 128/303 R |
| 4,065,816 | 1/1978 | Sawyer | 128/303 R X |
| 4,182,446 | 1/1980 | Penny | 623/2 X |
| 4,185,636 | 1/1980 | Gabbay et al. | 128/303 R X |
| 4,211,325 | 7/1980 | Wright | 623/2 X |
| 4,506,394 | 3/1985 | Bedard | 623/2 |
| 4,585,453 | 4/1986 | Martin et al. | 623/2 |

FOREIGN PATENT DOCUMENTS

| | | | |
|---|---|---|---|
| 207339 | 12/1967 | U.S.S.R. | 128/303 R |
| 0923542 | 5/1982 | U.S.S.R. | 623/2 |

OTHER PUBLICATIONS

"Hall-Kaster TM Prosthetic Heart Valve", 4/1979 Kastec Corp. brochure, p. 2.
"Bjork-Shiley Cardiac Valve Prosthesis with Convexo-Concave Disk", LC 1607, Apr. 1979, Shiley Sales Corp. brochure, p. 6.

Primary Examiner—William R. Cline
Assistant Examiner—Randolph A. Smith
Attorney, Agent, or Firm—Fitch, Even, Tabin & Flannery

[57] ABSTRACT

A two-piece heart valve holder engageable by a separate handle for positioning and rotating the heart valve. The holder includes a cylindrically-shaped plug member that has a recessed shoulder at one end and a V-shaped seat at the other end. Two passages extend through the plug member from the one end. A separate grip member includes two legs which extend through the passageways in the plug member. The two legs each include a base member. The two base members are hinged together with the legs biased outwardly, and each leg has an outwardly projecting valve-engaging foot at the distal end thereof. When the upper ends of the legs engage walls defining the passages, the legs are cammed outwardly so that the feet engage the edge of the valve body of the prosthesis to prevent its removal from the plug member. Once the prosthesis is sutured in place, the grip member is released by lifting a tab that extends upwardly from one of the base members.

10 Claims, 5 Drawing Figures

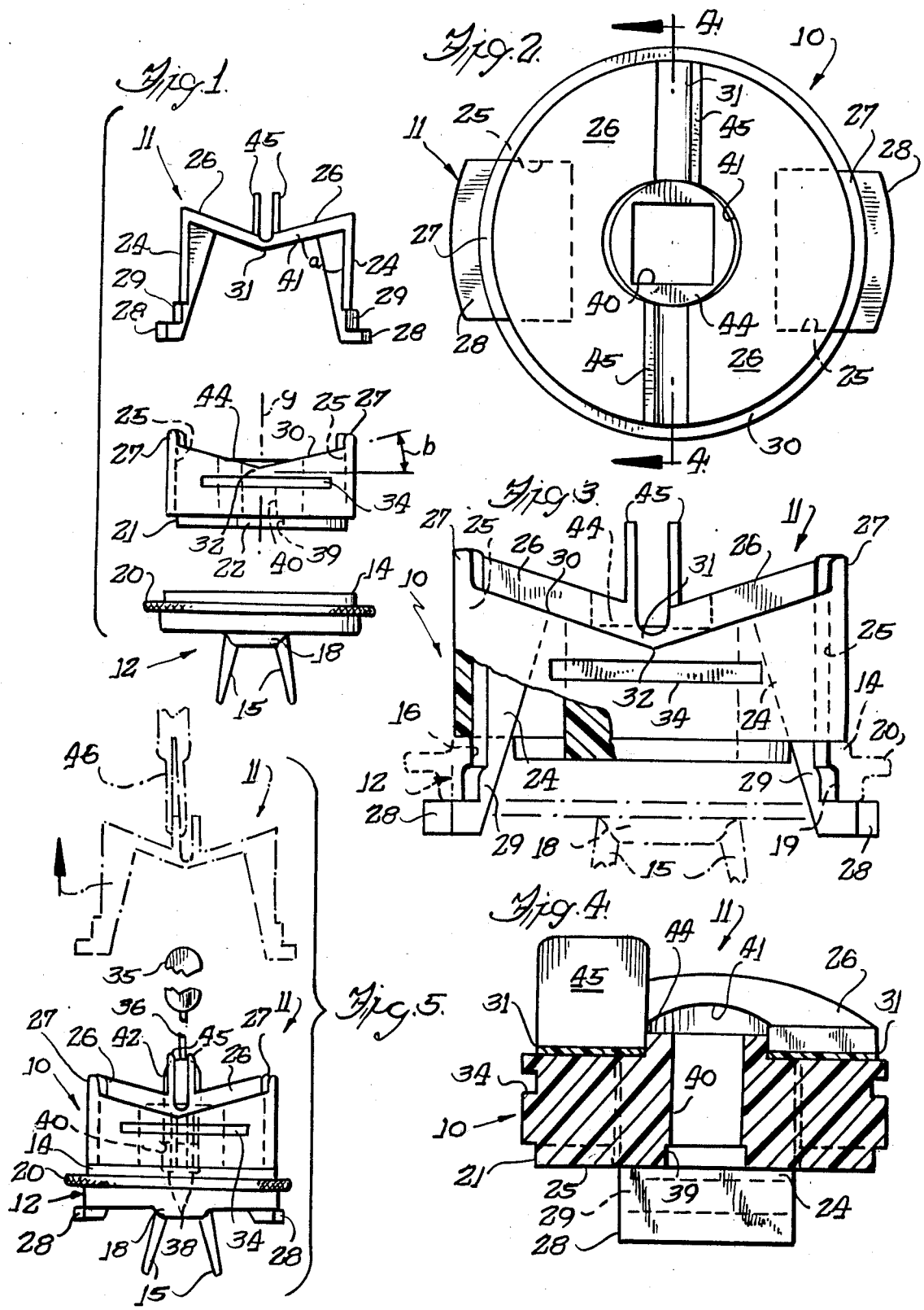

TWO-PIECE HEART VALVE HOLDER/ROTATOR

The present invention is directed to a device for holding a mechanical heart valve prosthesis both during shipment and during implantation.

BACKGROUND OF THE INVENTION

Surgically-implanted heart valve prostheses of the mechanical type have extended the life expectancy of many patients who had defective natural valves. Such prostheses are essentially check valves having a valve body that provides a blood flow passageway and an occluder, in the form of either one or two leaflets, that shifts to alternatively open the passageway, in response to blood flow in the circulation direction, and close the passageway, to prevent regurgitation of blood therethrough when the pumping action of the heart produces a localized back pressure. The heart valve body is generally formed from a rigid material, such as metal or pyrolytic carbon, and is commonly provided with a suture ring permanently secured thereto for attaching the valve body to the tissues of the heart.

To facilitate the implantation of heart valve prostheses, specialized holders have been developed that enable a surgeon to precisely position the heart valve and the suture ring within the heart passageway and to securely hold the assembly in place until suturing has been effected. It is desirable that such holders provide a quick, sure release of the sutured valve without placing undue strain on the tissue sutured to the prosthesis, and also that the holder be re-engageable with the valve body after the release thereof if repositioning of the valve is required.

For convenience, prostheses and their associated holders are frequently assembled by the manufacturer and shipped singly in sterile enclosures. During shipment of the assembly of the heart valve and holder, it is desirable that the assembly be stably held within the enclosure, and, more particularly, that the motion of the valve leaflets be sufficiently restricted so as to prevent any unnecessary load on the prosthesis due to the shifting of the leaflets during transportation.

SUMMARY OF THE INVENTION

Consequently, it is the principal object of the present invention to provide an improved device for holding a heart valve prosthesis both during shipment and during implantation.

More particularly it is an object of the invention to provide such a heart valve holder that facilitates precise positioning of the prosthesis for suturing and easy release of the prosthesis after suturing has been completed.

It is a further object of the invention to provide a heart valve holder that is re-engageable with the prosthesis after the release thereof so as to facilitate repositioning of the valve.

It is another object of the invention to provide a heart valve holder that restricts the movement of the heart valve leaflets during shipment.

These objects are met by a two-piece heart valve holder engageable by a separate handle for positioning and rotating the heart valve. The holder includes a cylindrically-shaped plug member that has a recessed shoulder at one end sized to fit within the inside surface of the body of the heart valve prosthesis. The other end of the cylindrical plug is in the form of a V-shaped seat. Two passages extend through the plug member parallel with the axis thereof, and extending upwardly from the periphery of the seat adjacent each of the passages is a wall or shoulder.

A separate grip member includes two legs, each sized in length to extend through the passageways in the plug member. The two legs each include a base member to which each leg is respectively connected at an angle inward from the outer edge of the base member substantially equal to the angle between each half of the V-shaped seat and a plane perpendicular to the axis of the plug member. The two base members are hinged together with the legs inherently biased outward at an angle complementary to that of the V-shaped seat so that the legs are substantially parallel when the grip is in its natural condition. Further, each leg has an outwardly projecting foot at the distal end thereof. To secure a heart valve prosthesis fitted onto the recessed shoulder of the plug member, the legs of the grip member are deflected inwardly and inserted into the passageways of the plug member. When the legs extend through the passageways, the feet are able to spring outwardly to engage the lower edge of the prosthesis. Additional camming force to bias the legs outwardly is provided by the walls on the seat adjacent to the passageways, thus maintaining the legs substantially parallel to the axis of the plug member and the feet on each leg in engagement with the edge of the valve body of the prosthesis to prevent its removal from the plug member.

The prosthesis, plug member and grip member are sterilized and shipped in this assembled condition in a hermetically sealed enclosure. Upon removal from the shipping enclosure, the plug member receives a handle for positioning and rotating the valve pursuant to its implantation. Once the prosthesis is sutured in place, the grip member is released by lifting a tab that extends upwardly from one of the base members. As the base members are lifted, the legs are forced inwardly and the feet are retracted from engagement with the edge of the valve body. The plug is disengaged from the valve by lifting the plug member with the handle.

Other features and advantages of the instant invention will become apparent upon reference to the following detailed description and accompanying drawings.

BRIEF DESCRIPTION OF THE DRAWINGS

FIG. 1 is an exploded elevational view showing the plug member, the grip member and the heart valve prosthesis;

FIG. 2 is a plan view of the plug member with the grip member inserted therein;

FIG. 3 is an elevational view in partial cross-section of the assembly of the plug member and grip member, with the heart valve prosthesis shown in phantom;

FIG. 4 is a cross-sectional view of the assembled plug member and grip member taken substantially along line 4—4 of FIG. 2; and FIG. 5 is an elevational view of the assembled heart valve prosthesis, plug member, grip member, and handle, with a removed grip member being shown in phantom.

DETAILED DESCRIPTION OF THE PREFERRED EMBODIMENT

Turning to the drawings, FIG. 1 shows a two-part holder and prosthesis that may be assembled in accordance with the present invention to facilitate the shipping and implantation of the prosthesis. The holder includes a plug member (which may be molded from polysulphone or a similar material), generally indicated by 10, and a grip member (preferably molded from nylon), generally indicated by 11, with the heart valve prosthesis indicated by 12. Although the operation of the prosthesis 12 and the constituent parts 10, 11, of the holder is not dependent upon their orientation (the prosthesis being oriented according to the anatomical configuration of the heart), for ease of explanation, the invention will be described with reference to the vertical orientation shown in the drawings.

As illustrated, the heart valve prosthesis 12 is substantially configured as described in Klawitter U.S. Pat. No. 4,413,894, which is herein incorporated by reference, and includes an annular valve body 14 having a central passageway therethrough. Pivotally disposed within the valve body 14 are a pair of leaflets 15 that are movable between open (as shown) and closed positions to either permit or restrict the flow of blood therethrough. The valve body 14 and leaflets 15 are made of a biocompatible, thromboresistant material, such as pyrolytic carbon. The central passageway of the valve body 14 has a generally circular interior wall 16 (best seen in FIG. 3), except in the region of a pair of diametrically-opposed flat surfaces (not shown) that extend into a pair of opposed depending standards 18, machined to provide for the pivotal interconnection between the leaflets 15 and the valve body 14. As illustrated, the interior wall 16 has an enlarged diameter at its lower end, indicated by 19 (FIG. 3). A suture ring 20 for attaching the prosthesis to the heart tissue is applied around the valve body 14 and typically comprises an annulus having an outer fabric layer that receives the sutures.

In keeping with the invention, the plug member 10 of the holder is substantially cylindrical in shape and includes a recessed shoulder 21 at its lower end sized to fit within the upper end of the interior wall 16 of the valve body 14. The shoulder 21 includes two diametrically-opposed flat sections, one of which is seen at 22 (FIG. 1), that complement the flat portions on the interior wall 16 of the valve body 14. When the heart valve prosthesis 12 is seated on the plug member 10, the interengaging flat sections on the prosthesis interior wall 16 and on the recessed shoulder 21 of the plug member 10 permit rotation of the plug member 10 and the prosthesis 12 in unison, while holding the suture ring 20 stationary.

To secure the plug member 10 to the prosthesis 12 once it has been seated thereon, the grip member 11 includes two diametrically-opposed legs 24 that are sized in length to extend through diametrically-opposed passages 25 in the plug member 10, such passageways 25 being parallel to the longitudinal axis Y of the plug member 10. Each leg 24 depends from a base member 26 and each has an outwardly projecting foot 28 that engages the lower edge of the valve body 14 of the prosthesis, as best seen in FIGS. 3 and 5. Immediately above the foot 28 on each leg 24 is a radial projection 29 that engages the underside of the land created by the enlarged diameter 19 of the interior wall 16 of the valve body 14.

As illustrated, the outer surface of each leg 24 is angled from its base member 26 at an acute angle a (See FIG. 1). To assure engagement of the feet 28 with the bottom edge of the valve body 14, the upper end of the plug 10 is shaped so as to not interfere with the relaxed configuration of the grip 11 in which the legs 24 are biased outwardly. As illustrated, the upper end of the plug member 10 terminates in a V-shaped seat 30 in which each half of the V extends upwardly from the horizontal at an angle b (FIG. 1) substantially equal to the complement of the angle a between each base member 26 and its respective leg 24. The two base members 26 are joined by a flexible hinge 31 that, when the legs 24 of the grip member 11 are inserted into the passageways 25 in the plug member 10, overlies the apex 32 of the V-shaped seat 30. In practice, the grip member 11 is unitary, with the hinge 31 formed by an area of reduced cross-section resilient material having a substantially U-shape, best seen in FIGS. 1 and 3. When the grip 11 is in its relaxed condition, the two legs 24 are substantially parallel, as shown in FIG. 1, and, when the legs 24 extend through the passageways 25 in the plug, the feet 28 will automatically move radially outwardly to engage the lower end of the valve body 14. Additional outward camming force is provided by the inner faces of shoulders or walls 27 that extend upwardly from the periphery of the seat 30 adjacent the passages 25. Contact of the base members 26 with the walls 27 ensures that the base members are maintained in their natural position, thus maintaining the legs 24 in parallel relation so that the feet 28 engage the lower edge of the valve body 14.

With the prosthesis 12 thus secured to the plug 10 by the grip member 11, the assembly is ready to be packaged and sterilized for shipment. When the grip 11 is in place, the legs 24 extend through the passageway of the prosthesis in such a manner that the leaflets 15 of the valve 12 are prevented from closing against the inside of the valve body 14 (See FIG. 4). This helps to reduce unnecessary loads on the prosthesis 12 prior to implantation and protects against possible damage caused by shock during shipment. In order to locate and secure the assembly within its shipping enclosure (not shown), the enclosure may contain a thin, C-shaped lock ring or plate (not shown), within which the assembly is captured by the facing edges of the "C". To this end, the exterior of the plug 10 includes two opposed slots or grooves 34, best seen in FIGS. 3 and 4, the slots 34 being formed perpendicular to the longitudinal axis Y of the plug 10 and being sized in width to frictionally capture the facing central edges of the lock plate.

In order to hold and position the assembly for implantation, a separate handle 35 (FIG. 5) is provided with each prosthesis 12. The handle 35 is preferably made of plastic or stainless steel and includes an elongated stainless steel shaft 36 that is easily bendable to suit the anatomical requirements of the implant site. The shaft 36 terminates in resilient prongs 38 whose hooked ends snap into the bottom of a square hole 40 that extends along the longitudinal axis Y of the plug member 10. Formed in the base members 26 of the grip member 11 is a circular hole 41 (FIG. 2) to provide access from above to the square hole 40 of the plug member 10 required for insertion of the handle 35. Because the hole 40 is square, the inserted handle 35 and the plug member 10 will rotate in either direction in unison upon the twisting of the handle 35 (which would not necessarily be the case if the hole 30 was circular in cross section and the plug member 10 resisted turning). The handle 35 is provided with a collar 42, having a flat lower end for abutting a flat upper surface of a cylindrical projection 44 on the otherwise V-shaped seat 30 of the plug 10, the upper opening of the square hole 40 being encircled by the projection 44.

In order to release the grip 11 after the prosthesis 12 is sutured in place, the grip member 11 is provided with an upwardly projecting tab 45. Preferably, one such tab 45 is provided on each base member 26. As illustrated, the tabs 45 are disposed diametrically on the grip 11 along opposite sides of the hinge 31. Release of the grip 11 is effected by holding the handle 35 (thus immobilizing the plug 10) and pulling on one of tabs 45 with a forceps 46 or the like (FIG. 5) to unseat the base members 26 from engagement with the inner surface of the walls 27 and cam the legs 24 inwardly, thus forcing the feet 28 out of engagement with the lower end of the valve body 14. At this point, the grip 11 may be discarded and the prosthesis 12 unseated from the plug 10 by lifting on the handle 35. If it is necessary to reorient the prosthesis 12 in situ after removal of the plug 10, the plug 10 with handle 35 still attached may be reseated in the prosthesis 12 by aligning the flats 22 on the recessed shoulder 21 of the plug 10 with the flats on the interior wall 16 of the valve body 14. The handle 35, plug 10 and prosthesis 12 may then be rotated in unison to reorient the prosthesis 12. After the prosthesis 12 is properly positioned, the plug 10 is withdrawn by the handle 35, and the plug 10 and the handle 35 may be discarded.

Thus it may be seen that a holder for a heart valve prosthesis has been provided that fully meets the above-stated objects. While the holder has been described in terms of a preferred embodiment, it will be understood that there is no intent to limit the invention by such disclosure. Rather, it is intended to cover all modifications and constructions falling within the spirit and scope of the invention as defined in the appended claims. For example, the tabs 45 may also be received in slots in the shipping enclosure to further stabilize the assembly during shipment. Further, while the preferred embodiment has a V-shaped seat, the seat may be of any shape that does not interfere with the relaxed, outwardly biased condition of the grip in which the legs will naturally engage the prosthesis upon the insertion of the legs through the passages in the plug.

What is claimed is:

1. A heart valve holder for holding a heart valve prosthesis during implantation, comprising, in combination:
    a plug means having opposite ends, one of which has a valve-engaging means and having passageway walls defining at least two passageways each extending in a generally axial direction between said opposite ends; and
    grip means including two legs extending through said passageways in the plug means, said legs each having a valve-engaging means at the free end thereof and a radially outward-facing surface adjacent a radially inward-facing surface of one of said passageway walls, said valve engaging means of said legs being movable between valve-engaging and valve-releasing positions in response to substantially axially directed movement of said grip means relative to said plug which effects camming engagement between said radially inward-facing surfaces and said radially outward-facing surfaces that cams said free ends radially inward.

2. The combination of claim 1 wherein said grip means further includes a leg-mounting plate having two hinged portions, each portion joined to said other end of a respective leg, said hinged portions being movable between first and second positions corresponding to said valve-engaging and said valve-releasing positions, respectively, and
    said plug means having a seating surface oriented at an angle to the axis so as to maintain said hinged portions in said first position.

3. The combination of claim 2 wherein said two portions are hinged together at a common hinge line, and at least one of said portions has plate-engaging means for applying an axial releasing force to at least one of said hinged portions to effect movement of said grip means which moves said leg to said valve-releasing position.

4. The combination of claim 1 wherein said grip means includes a generally flat base member extending radially inwardly from said other end of each of said legs, said base members being interconnected by resilient hinge means biased to maintain said base members in non-coplanar relationship, said base members being oriented at an acute angle to said radially outward-facing surface of the respective leg.

5. A device for positioning and holding a heart valve prosthesis during implantation comprising, in combination,
    substantially cylindrically-shaped plug means having a recessed shoulder at one end sized to fit within the inside surface of the body of the heart valve prosthesis, a seat at the end of the plug means opposite the recessed shoulder, the plug means having two passages therethrough extending between the two ends of the plug means and parallel with the longitudinal axis thereof, wall means projecting upwardly from the periphery of the seat adjacent each passageway, means for receiving a handle for positioning the prosthesis during implantation; and
    grip means including two legs, each sized in length to extend through the passageways in the plug means, each leg depending from a base member, the base members being resiliently hinged together, each leg having an outwardly extending end so that when the legs of the grip are placed through the passageways of the plug, the legs move radially outwardly, the outwardly extending ends engaging the edge of the heart valve prosthesis to secure the same to the plug means and being maintained in such position by a camming force exerted on the grip means by the projecting wall means.

6. The combination of claim 4 wherein the legs are inherently biased outward toward their prosthesis engaging position.

7. The combination of claim 4 in which at least one of the base members of the grip means includes an upwardly extending tab to facilitate retraction of the grip means upon pulling upwardly on the tab.

8. The combination of claim 4 wherein the plug means includes a hole coaxial with the axis of the plug for receiving the handle means, the base members of the grip means having a hole therethrough to provide access to the hole in the plug means.

9. The combination of claim 5 wherein the plug means includes two slots on the outside thereof and lying in a plane perpendicular to the axis of the plug means, for receiving locking and stabilizing means in the enclosure for shipping the assembled prosthesis and holder.

10. A device for positioning and holding a heart valve prosthesis during implantation comprising, in combination,
    substantially cylindrically-shaped plug means having a recessed shoulder at one end sized to frictionally engage the inside surface of the body of the heart valve prosthesis, a V-shaped seat at the end of the plug means opposite the recessed shoulder, the plug means having two passages therethrough extending between the two ends of the plug means and parallel with the longitudinal axis thereof, wall means projecting upwardly from the periphery of the seat adjacent each passageway, means for receiving a handle for positioning the prosthesis during implantation; and grip means including two legs, each sized in length to extend through the passageways in the plug means, each leg depending from a base member, the base members being hinged together, with the outer edge of each leg being angled inwardly from the outer edge of its base member at an angle substantially equal to the angle between each half of the V-shaped seat and a plane perpendicular to the longitudinal axis of the plug means, each leg having an outwardly extending end so that when the legs of the grip are placed through the passageways in the plug, the legs move radially outwardly, and the outwardly extending ends engaging the edge of the heart valve prosthesis to secure the same to the plug means and being maintained in such position by a camming force exerted on the grip means by the projecting wall means.

* * * * *

UNITED STATES PATENT AND TRADEMARK OFFICE
CERTIFICATE OF CORRECTION

PATENT NO. : 4,683,883
DATED : August 4, 1987
INVENTOR(S) : Richard L. Martin

It is certified that error appears in the above-identified patent and that said Letters Patent is hereby corrected as shown below:

Column 6, line 46, Change "4" to --5--.

Column 6, line 49, Change "4" to --5--.

Column 6, line 53, Change "4" to --5--.

Signed and Sealed this

Twenty-sixth Day of January, 1988

Attest:

DONALD J. QUIGG

Attesting Officer        Commissioner of Patents and Trademarks